US00PP08694P

United States Patent [19]

Hesse

[11] Patent Number: Plant 8,694

[45] Date of Patent: Apr. 19, 1994

[54] CHRYSANTHEMUM PLANT NAMED 'GOLDEN STATE'

[75] Inventor: Peter S. Hesse, Nipoma, Calif.

[73] Assignee: Clearwater Nursery, Inc., Nipoma, Calif.

[21] Appl. No.: 995,298

[22] Filed: Dec. 21, 1992

[51] Int. Cl.[5] ..... A01H 5/00

[52] U.S. Cl. ..... Plt./82.2

[58] Field of Search ..... Plt. 78, 82.2

[56] References Cited

U.S. PATENT DOCUMENTS

Plt. 67745 5/1989 Vanden Berg ..... Plt. 82.2
Plt. 5816 12/1986 Shoesmith ..... Plt. 82.2

*Primary Examiner*—Howard J. Locker
*Attorney, Agent, or Firm*—Arnold, White & Durkee

[57] ABSTRACT

The present invention comprises a new and distinct cultivar of Chrysanthemum, botanically known as *Dendranthema grandiflora,* and referred to by the cultivar name Golden State. The new cultivar is distinguished by its rich golden color, exceptional even flowering and spreading habit and its full crested anemone capitulum type. It displays superior shipping and keeping characteristics.

BACKGROUND OF THE NEW PLANT

Golden State, identified as originally coded P89-0280 was originated from a cross made by Peter S. Hesse in a controlled breeding program at Clearwater Nursery, 887 Mesa Rd., Nipoma, Calif. 98444, U.S.A.

The female parent of Golden State is the commercial variety Indio, U.S. Plant Pat. No. 6,774, and the male parent was Hopscotch, U.S. Plant Pat. No. 5,816.

Golden State was discovered and selected as one flowering plant within the progeny of the stated cross by Peter S. Hesse in Oct. 1989 in a controlled environment in Nipomo, Calif.

1 Drawing Sheet

The first act of asexual reproduction of Golden State was accomplished when vegetative cuttings were taken in April 1990 in a controlled environment in Nipomo, Calif. by Peter S. Hesse.

Horticultural examination of controlled flowerings of successive plantings has shown that the unique combination of characteristics as herein disclosed for Golden State are firmly fixed and are retained through successive generations of asexual reproduction.

Golden State has not been observed under all possible environmental conditions. The phenotype may vary significantly with variations in the environment such as temperature, light intensity and day length.

The following observations, measurements and comparisons describe plants grown in controlled environments in Nipomo, Calif. Unrooted cuttings were directly stuck into 6.5" pots and grown under the natural temperature and day length prevailing in March-May 1992.

The following traits have been repeatedly observed and are determined to be basic characteristics of Golden State, which in combination distinguish this Chrysanthemum as a new and distinct cultivar.

1. Flat capitulum form.
2. Anemone capitulum type.
3. Golden Yellow to Clear Yellow fully expanded outer ray florets.
4. Yellow Anemone disc with green eye.
5. An average of 6.75 flowers per break.
6. Diameter across the face of capitulum of 6.5 cm.
7. Exceptional upright to spreading habit with an average of 5.0 breaks after a single pinch.
8. Flowering response of approximately 59 days from the start of short days.
9. Relative easy in controlling plant height such that the finished height will range from 10 inches to 18 inches from the bottom the pot size and market requirements.

DESCRIPTION OF THE PHOTOGRAPH

The accompanying photograph shows typical inflorescence and leaf characteristics of Golden State, with the colors being as nearly true as possible with illustrations of this type. The photograph shows Golden State grown as a pinched spray pot mum with 5 cuttings in a 6.5" pot.

DESCRIPTION OF THE PLANT

Of the commercial cultivars known to the inventor, the most similar in form, color, and habit to Golden State are the cultivars Yellow Tara, U.S. Plant Pat. No. 6,774, and Hopscotch, U.S. Plant Pat. No. 5,816. Reference is made to Table I which compares certain characteristics of Golden State with the cultivars Yellow Tara and Hopscotch.

TABLE I

| CHARACTERISTIC | HOPSCOTCH | GOLDEN STATE |
|---|---|---|
| CAPITULUM FORM | FLAT | FLAT |
| CAPITULUM TYPE | DAISY | ANEMONE |
| DIAMETER ACROSS FACE OF CAPITULUM | 9.5-11.5 CM | 6.5 CM |
| BRANCHING PATTERN | UPRIGHT & SPREADING | UPRIGHT & SPREADING |
| BREAKS/PINCH | 4.4 | 5.0 |
| HEIGHT IN A 6.5" POT | 16-18 INCHES | 16-17 INCHES |
| DISC FLORET | MOSTLY YELLOW GREEN 149 A | EDGE BEGIN W/9A GRADUATING TO YELLOW GREEN 144A |
| # DISC FLORETS | 183.2 | 171 |
| LENGTH OF DISC FLORETS | .64 CM | 1.43 CM |
| RAY FLORET COLOR | FRONT: GOLDEN YELLOW 9A BACK: PALE YELLOW 6A | FRONT: GOLDEN YELLOW 9A BACK: PALE YELLOW 6B |
| # RAY FLORETS | 32.6 | 19 |
| SHAPE OF RAY FLORETS | ELLIPTIC | ELLIPTIC |

TABLE I-continued

| | | |
|---|---|---|
| LENGTH OF RAY FLORETS | 3.85 CM | 3.65 CM |
| WITH OF RAY FLORETS | 1.43 CM | 1.09 CM |
| # OF FLOWERS/ BREAK | 6.7 | 6.75 |
| LEAF COLOR | FRONT: 147 A BACK: 147 B | FRONT: 147 A BACK: 147 B |
| MATURE LEAF LENGTH | UP TO 10.2 CM | UP TO 12.55 CM |
| MATURE LEAF WIDTH | 5.95 CM | 8.78 CM |
| CONTROLLED RESPONSE | 8.5 WEEKS weeks: MT (requires nine (9) weeks for flowering: medium vigorous grower) | 8.5 WEEKS |

| CHARACTERISTIC | YELLOW TARA |
|---|---|
| CAPITULUM FORM | FLAT |
| CAPITULUM TYPE | ANEMONE |
| DIAMETER ACROSS FACE OF CAPITULUM | 6.5 CM |
| BRANCHING PATTERN | UPRIGHT & SPREADING |
| BREAKS/PINCH | 4.4 |
| HEIGHT IN A 6.5" POT | 16–17 INCHES |
| DISC FLORET | EDGE BEGIN W/ 9A GRAD. TO 144 A |
| # DISC FLORETS | 111.8 |
| LENGHT OF DISC FLORETS | 1.19 CM |
| RAY FLORET COLOR | FRONT: PALE YELLOW 5B BACK: PALE YELLOW 6B |
| # RAY FLORETS | 17 |
| SHAPE OF RAY FLORETS | ELLIPTIC |
| LENGTH OF RAY FLORETS | 3.09 CM |
| WIDTH OF RAY FLORETS | 0.95 CM |
| # OF FLOWERS/ BREAK | 9.4 |
| LEAF COLOR | FRONT: 147 A BACK: 147 B |
| MATURE LEAF LENGTH | UP TO 9.6 CM |
| MATURE LEAF WIDTH | 8.90 CM |
| CONTROLLED RESPONSE | 8.5 WEEKS weeks: MT (requires nine (9) weeks for flowering: medium vigorous grower) |

Golden State is similar to Yellow Tara in having a flat capitulum form and anemone capitulum type. Hopscotch has a much larger diameter across the capitulum than Golden State and has the daisy capitulum type. Golden State has strong stems, and an exceptional even flowering and spreading habit, whereas Hopscotch has strong stems and a less even and more upright habit. Yellow Tara, Hopscotch and Golden State are approximately the same height; however Yellow Tara is less vigorous than Golden State. Golden State averages more breaks per pinch, than either Yellow Tara or Hopscotch. Therefore, Golden State makes an exceptionally full floriferous pot.

Hopscotch has more disc florets, than Golden State, which in turn has more than Yellow Tara. The length of the disc florets is greatest for Golden State and less for Hopscotch and Yellow Tara, which makes Golden State an exceptional full crested anemone. The front ray floret color for Golden State is similar to Hopscotch but the back of the ray floret is different. Golden State has a much darker yellow ray floret than Yellow Tara. Hopscotch has more ray florets than Golden State, whereas Golden State has a few more than Yellow Tara. The length of the ray florets is similar for Hopscotch and Golden State, but Golden State has longer ray florets than Yellow Tara. The width of the ray florets for Golden State is intermediate between Hopscotch and Yellow Tara. Yellow Tara has more flowers per break (side stem) than either Hopscotch or Golden State. Leaf color for all three varieties is the same. Golden State has longer leaves than either Hopscotch or Yellow Tara. Hopscotch has narrower leaves than either Golden State or Yellow Tara. The response time on the bench of all three varieties from the start of short days is similar; 56–59 days. Golden State has an excellent root system, similar to Hopscotch, but much better than Yellow Tara. Golden State displays superior shipping and keeping characteristics.

The following lists the characteristic traits of the new cultivar Golden State.

Classification:

*Botanical.*—*Dendranthema grandiflora* cv. name Golden State.

*Commercial.*—Flat anemone to be grown primarily as a Spray/CBR or Disbud pot mum.

INFLORESCENCE

A. Capitulum:

*Form.*—Flat.

*Type.*—Anemone.

*Diameter across face.*—Average of 6.5 cm.

B. Corolla of Ray Florets:

*Color (general tonality from a distance of three meters).*—Yellow.

*Color.*—Front fully expanded outer ray floret: 9A. Back fully expanded outer ray floret: 8A. Disc floret color edge begins with 9A to Center 144A.

PLANT

A. General Appearance:

*Height.*—When grown in a 6.5" pot with 1–4 applications of B-9 the total plant height from the bottom of the pot may be maintained at 16–18 inches. When grown in a 4.5" pot with 1–4 applications of B9 the total plant height from the bottom of the pot may be maintained at 10–12 inches.

*Branching pattern.*—Upright and spreading with an average of 5.0 breaks when grown with one pinch.

B. Foliage:

*Color (upper surface).*—147 A.

*Color (lower surface).*—147 B.

REPRODUCTIVE ORGANS

A. Androecium: Present in disc florets only, scant pollen.

B. Gynoecium: Present in ray and disc florets.

What is claimed is:

1. A new and distinct cultivar of Chrysanthemum plant, substantially as herein shown and described, and being characterized by its rich golden yellow ray floret color, full-crested anemone capitulum type, and its exceptional even flowering and spreading habit.

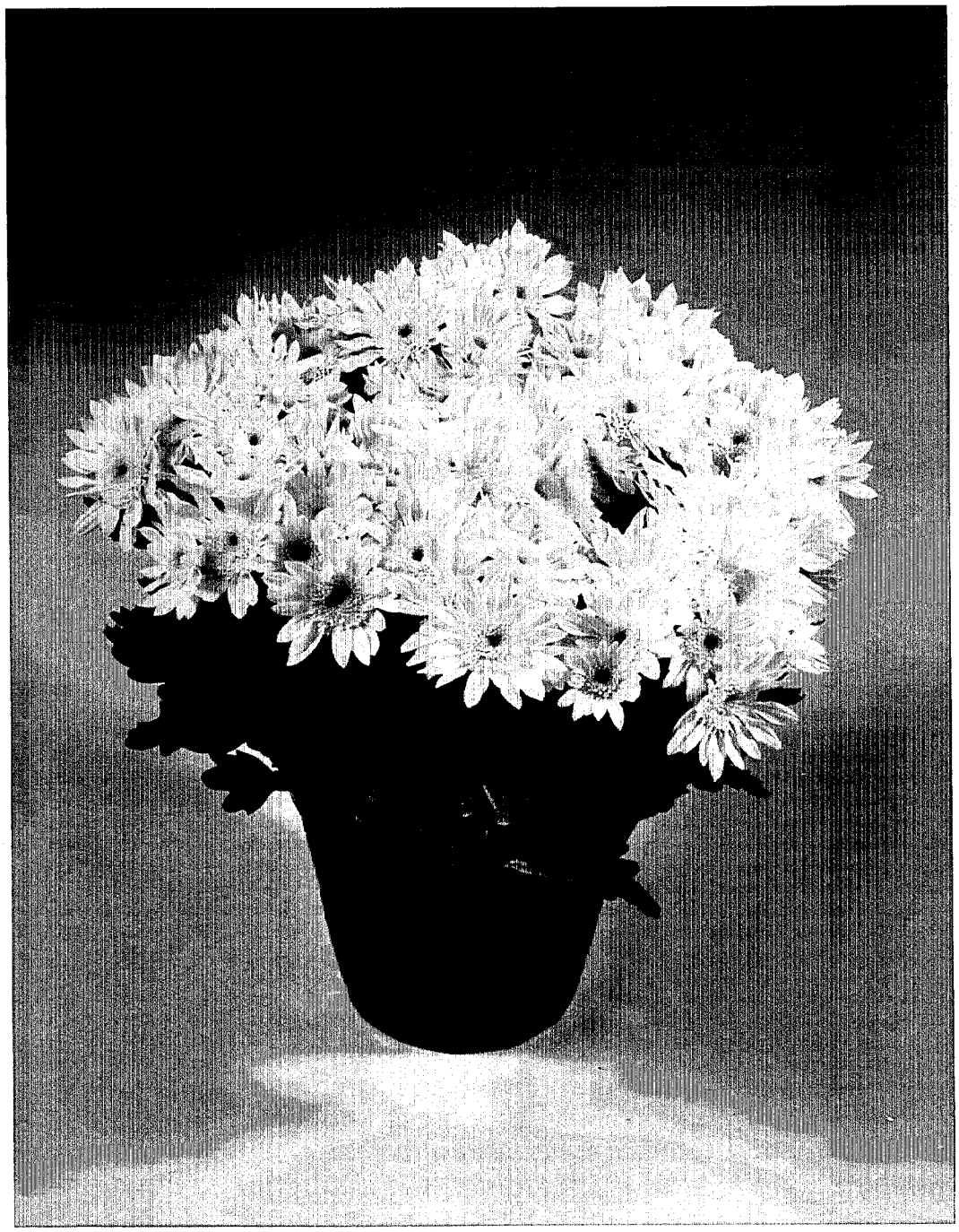

* * * * *